United States Patent [19]

Pendleton

[11] 4,086,058

[45] Apr. 25, 1978

[54] ANALYTICAL SYSTEM, REAGENT DISPENSING AND SAMPLING APPARATUS AND METHOD

[76] Inventor: Betty Pendleton, 1226 S. 18th Ave., Birmingham, Ala. 35205

[21] Appl. No.: 704,606

[22] Filed: Jul. 12, 1976

Related U.S. Application Data

[63] Continuation-in-part of Ser. No. 482,628, Jun. 24, 1974, abandoned.

[51] Int. Cl.² .............................................. G01N 31/00
[52] U.S. Cl. ................................ 23/230 B; 23/253 R; 210/24; 73/61.1 R; 356/39
[58] Field of Search ............. 23/230 B, 230 R, 253 R, 23/259; 210/24, 25, DIG. 23; 356/39; 73/61.1 R

[56] References Cited

U.S. PATENT DOCUMENTS

| | | | |
|---|---|---|---|
| 3,436,344 | 4/1969 | Canning et al. | 210/24 X |
| 3,476,515 | 11/1969 | Johnson et al. | 23/230 R |
| 3,676,080 | 7/1972 | Richterich | 23/253 R |
| 3,728,079 | 4/1973 | Moran | 23/253 R |
| 3,799,744 | 3/1974 | Jones | 23/253 R |

*Primary Examiner*—Norman Yudkoff
*Attorney, Agent, or Firm*—George R. Douglas, Jr.; Sherman Levy

[57] ABSTRACT

An improved system and method of analytical testing for medical purposes including reagent and sample measuring and dispensing by means and steps of forming matrixes of tubes or containers for specimens, applying the specimen to a spectrophotometer for quantitation, recording the results, then routing the chemicals and biological materials to an ion exchanger for final disposition for elimination of problems of pollutants and sediment collection.

9 Claims, 6 Drawing Figures

ANALYTICAL SYSTEM, REAGENT DISPENSING AND SAMPLING APPARATUS AND METHOD

CROSS REFERENCE TO INFORMATION AND REFERENCES

This application is a continuation-in-part application of my copending application Ser. No. 482,628 filed June 24, 1974, now abandoned.

A search of prior art apparatus and methods not anticipative or of direct relevance to the present invention are the following U.S. Patents:

| Patent No. | Name |
|---|---|
| 3,327,535 | Sequeira |
| 3,450,501 | Oberhardt |
| 3,489,525 | Natelson |
| 3,544,272 | Vaills |
| 3,572,552 | Guinn |
| 2,865,303 | Ferrari, Jr. et al |
| 2,935,028 | Ferrari, Jr. et al |
| 3,143,393 | De Seguin Des Hons |
| 3,241,432 | Skeggs et al |
| 3,520,660 | Webb |
| 3,560,161 | Webb |
| 3,622,279 | Moran |
| 3,188,181 | Peterson |
| 3,536,449 | Astle |

BRIEF SUMMARY OF THE INVENTION

The present invention relates to new and improved automated reagent adding, dispensing and sampling apparatus and method thereof; more particularly, the present invention is an apparatus and method useful in environmental quality testing; and more particularly, the invention is directed to and relates to a new and improved analytical instrument. The instrument is an apparatus providing for reagent adding and sampling steps in measuring and testing systems.

One of the advanced features of the present invention is to provide an ion exchanger for receiving wastes, chemical washes, and detoxification of solutions after use and operation of measuring and testing apparatus, in which the ion exchanger by use of carbon absorption, ion exchange resins, and the like, the wastes are ionically treated to neutralize the wastes, etc., so that they may be washed down the sewer without presenting any problems of pollutants and sediment collecting in the sewer.

FIELD OF THE INVENTION

An underlying and pervasive concept of the present invention is to provide a method and apparatus for testing of blood for multiple medical chemical tests which result in quicker or faster medical patient care at substantially lesser costs with simplistic equipment.

By use of the devices of the present invention, a method is provided which may be described as one forming a product of the manual and completely automated testing equipment. Results are obtained much faster than with manual methods of the prior art, but not quite as fast as with automated devices, and at costs far below that of automated devices.

It must be realized that the analytical instruments of prior art systems that are automated have the following broad characteristics:

|  | Costs $ in K's | Test Rate/Hour | Other |
|---|---|---|---|
| AGA Auto Chemist | 430 | 3000 | (8 in entire world; weight 4 tons - sq.ft.) |
| Technicon SMA 12.60 | 70 | 760 | One room required, most in use. |
| Hycel Mark 10 | 60 | 400 | 6' × 8'; needs floor drain. |
| Present Device | 6 | 144 | 3' × 4'; floor or shelf model. |

(Other devices about $28-K-70K, manufactured by Beckman DSA-560; Dupont ACA; Vickers 300, etc.)

The above devices that are completely automated are for high volume testing and located in centers to which blood collected at the local level of a doctor's office, clinic, or hospital, is sent via air mail, or air freight throughout the country to one such center as the United Medical Laboratories, Portland, Oreg. Reports may be sent back by air mail, telex, facsimile, or telefax systems. The centers that may house lesser expensive automated instruments are used to do the laboratory testing for many doctors in the surrounding community. In the latter case, the blood is simply picked up by messenger once daily, and test results are later sent back to the doctors, either by mail or messenger-delivery in from 1 to 5 days.

BACKGROUND OF THE INVENTION

An advantage of the present invention therefore is economy in cost, space and time for both doctor and patient.

Because of the small size, low cost, speed and simplicity, it can be located in a doctor's office or small clinic. With the patient nearby, testing can begin immediately. Test results can be given to the doctor for his rapid interpretation, decision and report to the patient as whether to hospitalize, treat of release while the patient is in the office.

The invention is created to test and report laboratory results on six patients every 30 minutes.

Further, it is an advantage and object of the invention to propose a method of testing that employs:

a. manual multiple and simultaneous serum sampling;

b. motor assisted, multiple and simultaneous reagent addition, (or automatic reagent dispense);

c. conventional photoanalytical quantitation, and recording of results;

d. treatment of chemical solutions used, to avoid or to reduce pollution of water supply.

BRIEF DESCRIPTION OF THE DRAWINGS

The above and other objects and advantages of the invention will become apparent upon full consideration of the following detailed description and accompanying drawings in which:

FIG. 6 is in part a perspective and part block diagram of a waste treatment system used in the arrangement of the invention.

DETAILED DESCRIPTION OF THE PREFERRED EMBODIMENT

Figure 1:
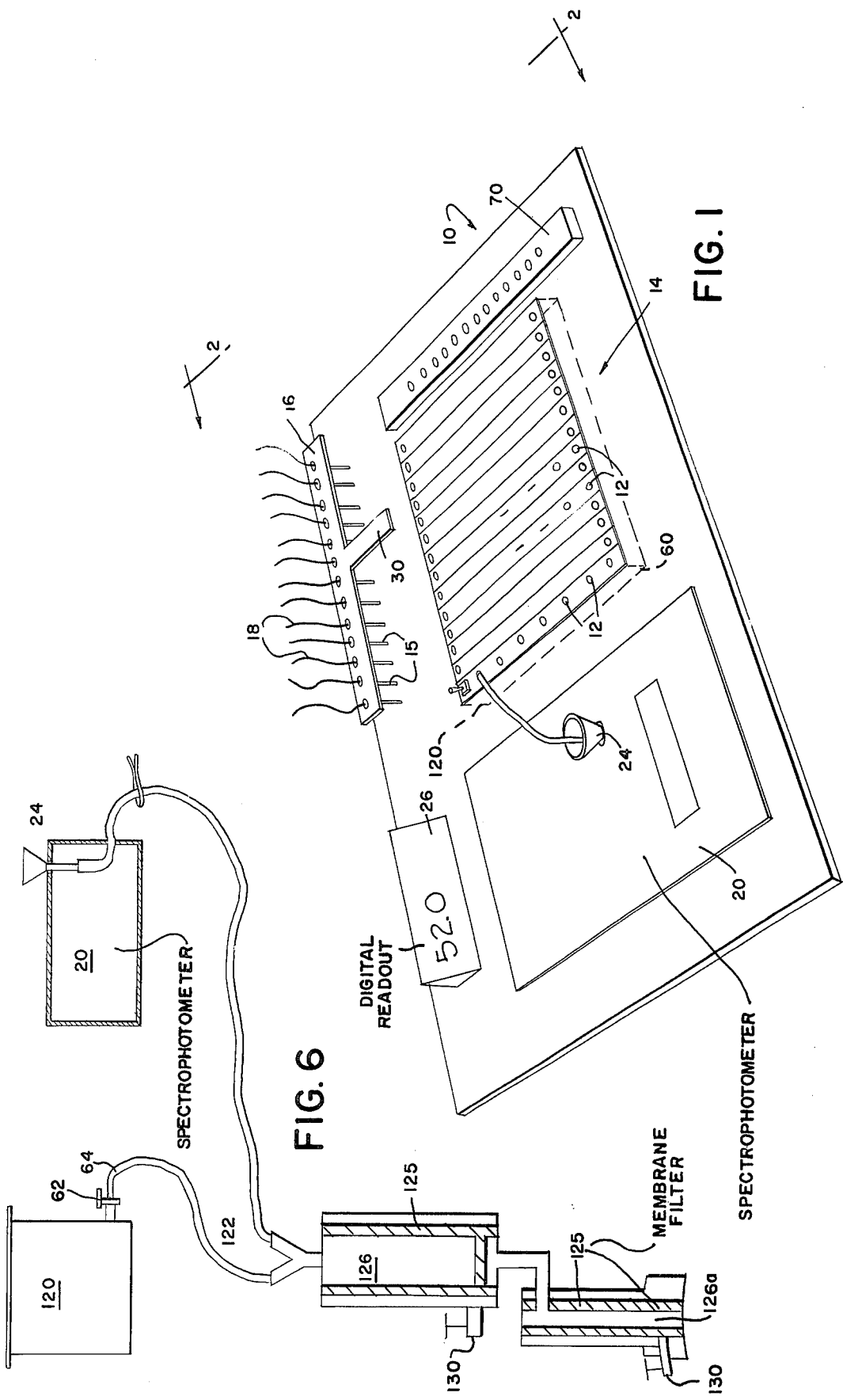
FIG. 1 is an isometric or perspective upper view of a preferred embodiment of the present invention showing the apparatus and method of a reagent dispenser and serum sampler.

Referring now to the drawings embodying the invention, there is shown a sampling apparatus 10 showing the relative position and locations of the various elements constituting the preferred embodiment. FIG. 1 further shows tops of the sampling tubes 12 holding sera to be tested in the form of an array of tubes 14 and which thus form a matrix system of tubes to be tested. The tops of tubes 12 each are positioned to receive fixed amounts of reagents which are dispensed by entry ports means 15 of holder 16. The top of a typical reaction tube is shown and tubing 18 leading from reagent pumps (not shown in FIG. 1) are shown. A spectrophotometer 20 is provided on the panel apparatus 10 and it includes a funnel at 24 leading into a flow-through cuvette 124 (FIG. 6) (not shown in FIG. 1). A digital readout of concentration is shown as a digital read-out device 26.

For dispensing metered amounts of reagents according to the method of the invention, the holder 16 may be supported by a handle 30. The holder 16 is manually positioned over a selected one of the array 14 or rows of reaction tubes 12 in the configuration. The holder 16 is then lowered manually by the handle 30 so that all the entry ports or means 15 enter the tops of each of the test tubes 12 across the row of the array 14 to be dispensed. Each of the flexible tubing 18 communicates with one of a group of reservoir or containers located in trays (not shown in FIG. 1) but described below.

Figure 2:
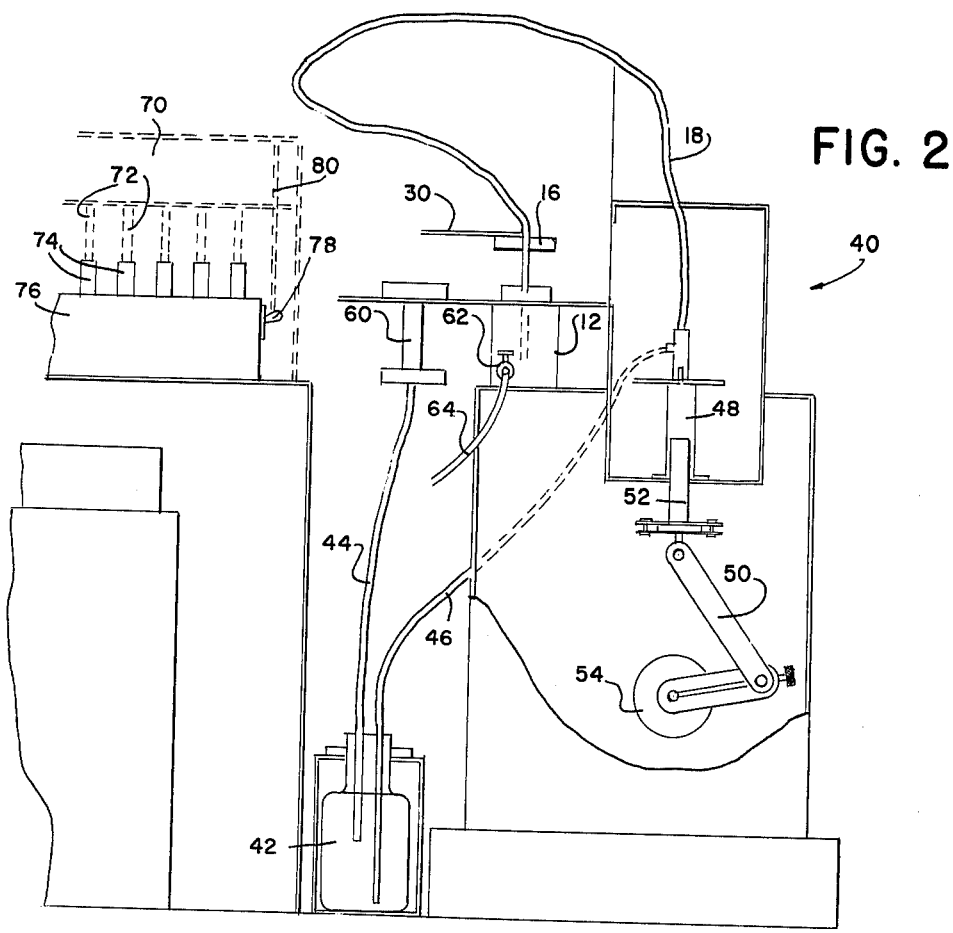
FIG. 2 is a side view of the apparatus referred to in FIG. 1 and shown taken along lines 2—2 of FIG. 1.

FIG. 2 shows a dispenser 40 having a typical reservoir or container 42 shown in the form of a large bottle containing a selected and specific reagent. The container 42 may be one of a multiplicity of such reservoirs deployed beneath the table apparatus shown in FIG. 1. Two flexible tubings 44, 46 are shown entering the top of reservoir 42. The tubing 46 is the means by which the reagent egresses under suction produced by a syringe 48. Back flow is prevented by valve 43. Tube 44 is for the purpose of readmitting reagent into the reservoir 42 for those operations in which that particular reagent is not required for tests. A crank 50 is shown connected to a plunger 52 and driven by a motor drive 54. This is the means by which a metered amount of reagent may be drawn from reservoir 42 through tubing 46 during each stroke of the plunger 52. Discharge from the syringe 48 is carried through tubing 18 into one of the reaction tubes 12 into which the ends of the tubing 18 has been inserted by means of holder 16 by use of the handle 30. The reaction tubes 12 are located within waste tray 120 or receptacle 60.

A receptacle 60 connected to tubing 44 is positioned so that the tubing 18 may be alternatively dropped into receptacle 60 to return reagent in those instances where the particular reagent stored in one of the reservoirs 42 is not to be used in a given particular test.

After one or more reagents has been dispensed into a particular reaction tube 12 containing sera, the resulting colored mixture may be drawn off through tubing directly through the funnel 24 shown in FIG. 1 into a cuvette for analysis by the spectrophotometer 20.

By means of tubing 64 and a valve 62, removal of waste chemicals from washing and priming of pumps is provided. Tubing 64 leads waste through a deionizer of conventional construction. Receptacles 60, each communicating through tubings 44 to the reagent reservoirs 42, are representative of the series that is actually provided. This is the means by which a reagent may be returned to a reservoir for reuse. This arrangement provides a simple method by which reagents which are not required for a particular test may be returned to the reservoirs. The operator is responsible for removing the tubing 18 from the holder 16 and placing it into one of the access openings provided in receptacle 60.

Also shown in a portion of the sampling mechanism 70, and this consists of a row of syringes 72 positioned over a corresponding row of serum tubes 74 positioned in holder 76. A handle 78 connects with a micro switch (not shown) located within the holder 76. A rod 80 protrudes or extends from the top of the sampling mechanism 70 and is positioned just touching handle 78. The rod 80 is configured so that as the multi-syringe sampler is inserted into the serum tubes 74, the rod 80 impacts with the handle 78 to thus operate and close the microswitch to start operation of the dispenser pump 48–54.

Figure 3:
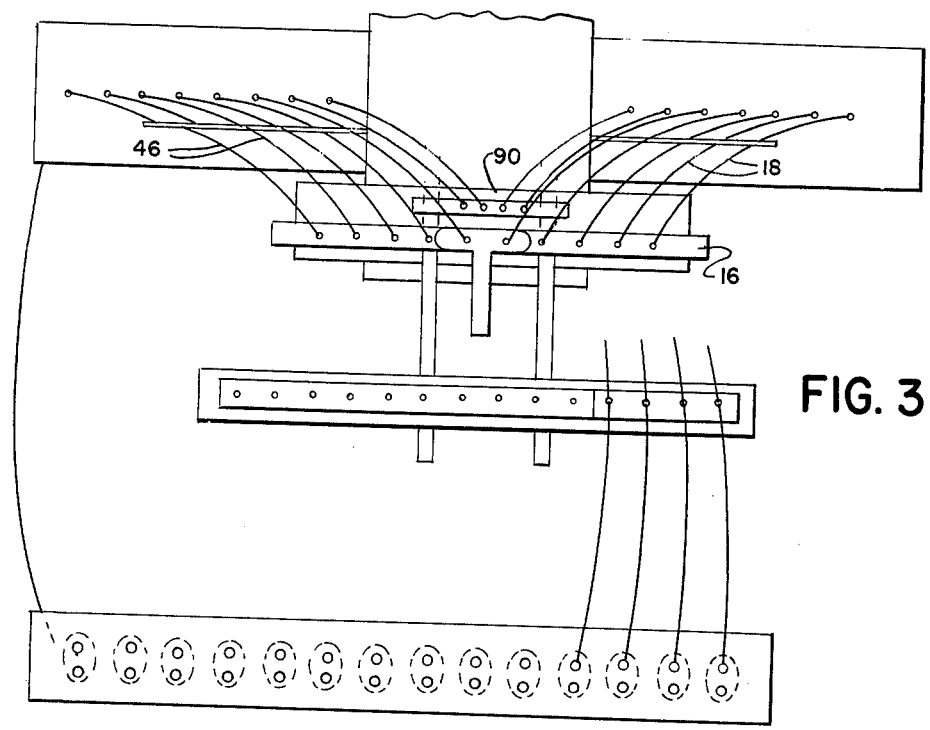
FIG. 3 is a top or plan view of the dispenser shown in FIGS. 1 and 2.

FIG. 3 is a top view of the dispenser in which tubing 18 extend from the output ports of the dispenser pump 48–54. The tubing 18 are shown entering the holder 16, or alternatively, some going into the reservoirs through a separate set of access holes 90a in holder 90. The holder 16 is shown positioned over the waste tray 120.

Also shown are access ports for the receptacle 60 to which are connected pieces of tubing 44 shown entering the tops of the reagent reservoir 42 (FIG. 2). To the left of the drawing is a typical piece of tubing 46 which supplies reagent to the dispenser pumps from each of the reservoir bottles.

Figure 4:
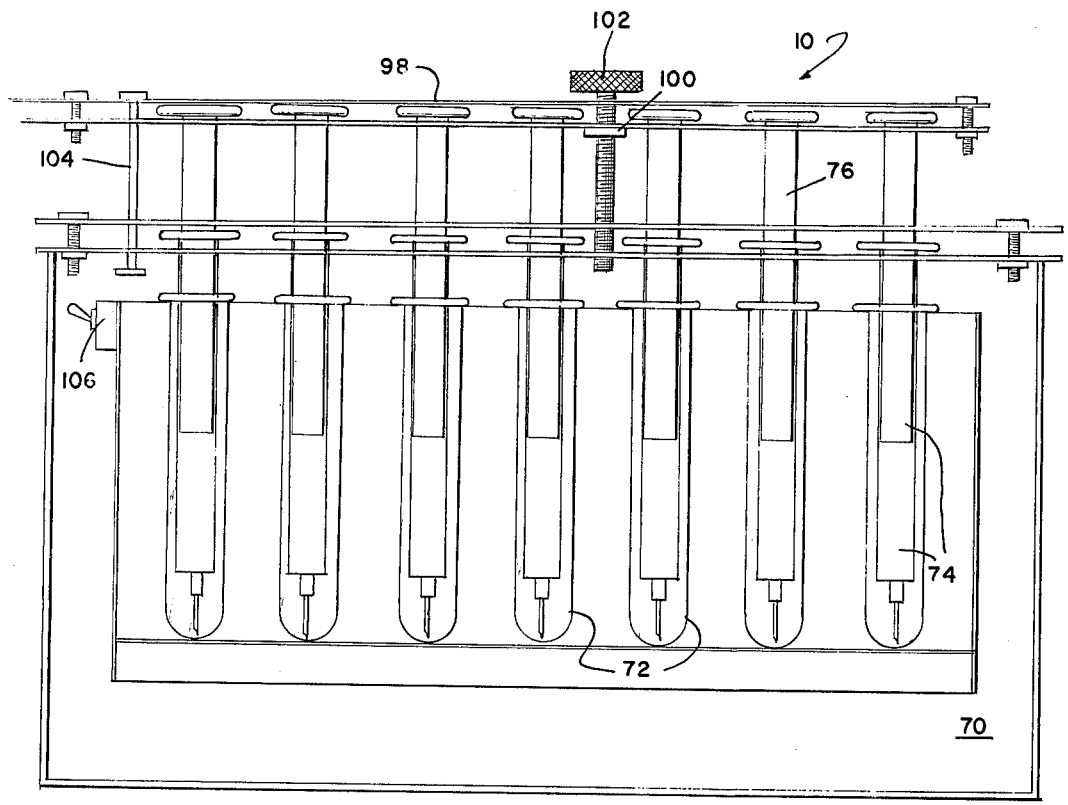
FIG. 4 is a front elevational view of a sampler.

FIG. 4 is a detailed drawing of a sampler designed to multiple draw uniform sera samples from a multiplicity of reaction tubes. A rack 70 is shown which holds a set of reaction tubes 72. Into the test tubes 72 are inserted the ends of a set of syringes 74. Within the syringes are placed plungers 76, fastened to a plate 98.

The plate 98 is provided with a threaded aperture 100 which passes a threaded rod 102 arranged so that as the threaded rod 102 is rotated the plate 98 and plungers 76 move up and down. Upward movement of plate causes filling of the syringe, while downward movement empties the syringe.

Connected to one end of the plate 98 is a metal rod 104 positioned above a portable micro switch 106 so that the dispenser cycle may be initiated at the end of the sampling cycle.

Figure 5:
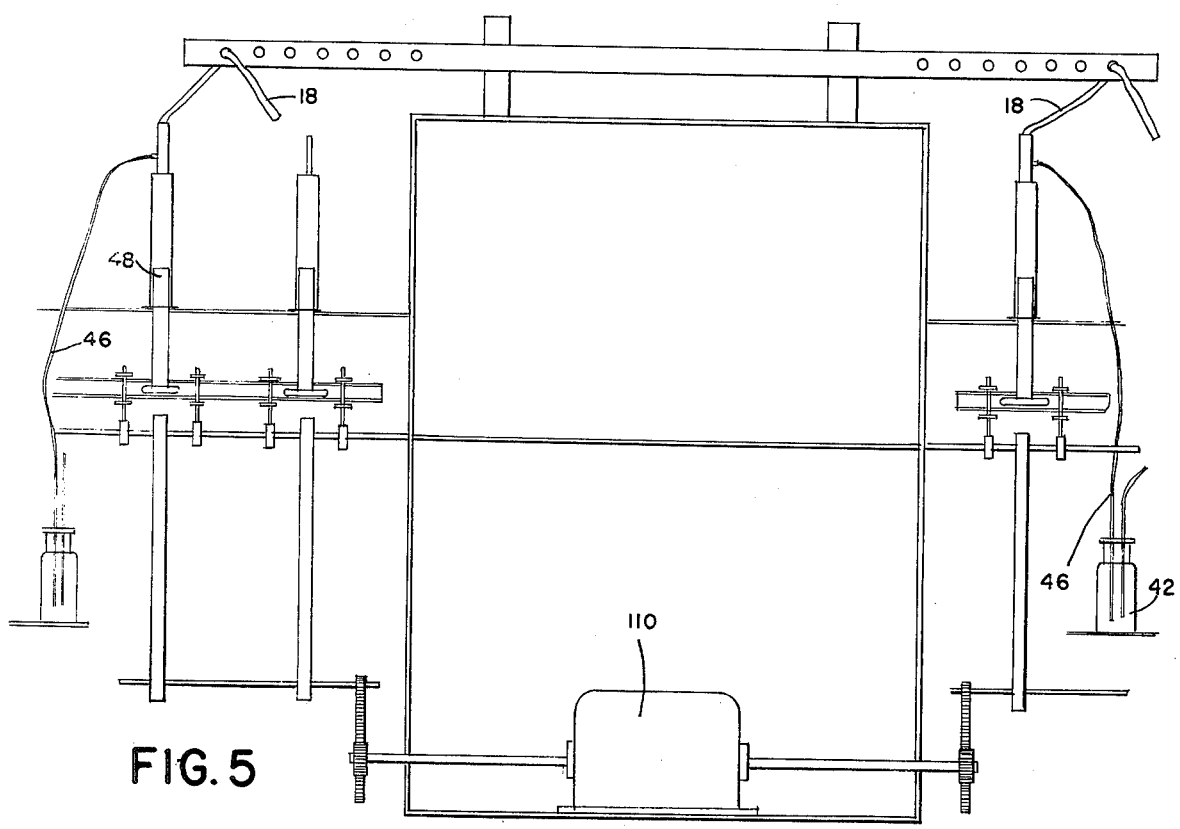
FIG. 5 is a front elevational view of the automatic or semi-automatic multiple dispenser.

FIG. 5 is a front view of the multiple dispenser in which a motor 110 is shown coupled to a set of dispensing pumps. All pumps are actuated by the motion of a common rod connected to a set of cranks. The cranks are shown coupled to a set of plungers 48 inside the pumps.

A typical one of a set of reagent reservoirs is shown at 42 connecting through flexible tubing 46 to the input of a typical pump.

FIG. 6 shows the tubing connections from the waste tray 120 and from the flow-through cuvette 124 joining at a Y connection 122 which empties into the ion exchanger 126. The purified waste which leaves the ion exchanger 126 is shown passing to the sewer connection 130.

DESCRIPTION OF THE OPERATION

To prepare the devices for use, the reservoir bottles are first charged with appropriate reagents. The dispenser is turned on and tubing and pumps are filled with reagents. The excess from the priming runs off via waste tray to ion exchanger.

The sera from six patients and one control fill one of each of the seven syringes in the sampler. A small volume of serum from each syringe is added to seven reaction tubes in a holder by one or more revolutions of the threaded rod. The sampling procedure is repeated until 12 sets of seven reaction tubes have received a definite volume of sera. At the end of the sampling cycle the reagent dispenser is actuated.

Spacings between syringes, tubing ends and reaction tubes are, of course, identical.

The optimum number of tests is done by addition of all reagents to all the sera samples of each patient. If a test or tests (of the group of tests being run) is not needed, on any one patient, the reagent for the test or tests is not added to the serum in the reaction tube, but directed back to its reservoir via receptacles 60. This allows versatility of the apparatus and economy of the reagent.

As the dispenser is actuated, the handle 30 enables placement of holder 16 to insert tubing 18, bearing reagents from the pumps, into an array of reaction tubes containing measured amounts of one patient's serum. The reagents are delivered and all tests on one patient begin. Holder 16 then is moved and all reagents are added to the next row of reaction tubes containing sera from the second patient. This procedure is repeated at timed intervals until all reaction tubes contain reagent. At the end of this dispensing and at timed intervals, the contents of each tube is introduced into the flow-through cuvette of a spectrophotometer where it is photoanalytically viewed, quantitated, recorded and passed to the ion exchanger.

Further versatility can be accomplished. For example, some tests require elevated temperatures and in this event reagents can be measured out by use of the dispenser, allowed to attain the required temperature and then a volume of serum added to the reagents by use of the sampler. Some reagents can be measured, dispensed, and held until needed. For instance, the reagent for a hemoglobin test can be dispensed and held for later use. The complete system could be easily placed in an enclosed truck and moved into remote areas for on the spot testing of populations in areas with little or no facilities for medical care. A small refrigerator would be required for some reagents. A doctor and nurse could take history and do physical exam, a person could collect and prepare blood, and an operator could use the analytical system presented here, to test and report lab results for a mobile clinic. A 110 volt A.C. power plug would be needed.

Waste Treatment

In FIG. 6 is that portion of the device devoted to the purification of waste matter. In the preferred embodiment, this waste may originate in the waste tray 120 as an overflow from the dispensing operation, or may come from the flow-through cuvette 124 located in the spectrophotometer 20.

Ion exchangers 126 and 126a receive waste piped in from the wash and priming tray or alternatively through a separate tubing from the flow-through cuvette 124 in the spectrophotometer 20. Waste liquids from both sources enter at a Y-connection 122 into an ion exchanger 126 containing ion exchange resins in a membrane filter 125. The principles of the ion exchanges 126 and 126a are well known from the prior art. The use of an ion exchanger 126 as an integral part of the dispensing device herein described results in an improved dispenser.

Ion exchange resins used on ion exchanger unit 126 are contained in a membrane filter 125 or cartridge, and may be used to render the chemical solution from the testing procedure less corrosive and toxic. The type of resins selected for use depend upon which chemicals and tests are being conducted and thus on the chemicals contained in the reagents used. For the routine testing most frequently used, a cartridge containing a mixed bed resin plus Chelex-100, a requistered trademark, is used. A mixed bed resin consists of equal quantities of a strong base ion exchange resin and a strong acid cation exchange resin. Such a mixture is AG5-1-$\times$8 resin available from Bio-Rad Laboratories, Richmond, Calif.

Chelex-100 resin is added for removal of copper, iron, other heavy metals as well as alkaline earths. After passage of the chemical solution through the resins in the cartridge, the resultant solution can and may be safely washed down the drain into the sewage system.

Other well known resins for achieving the removal of these items may be used.

A second cartridge of resins in ion exchanger 126a is added, in some applications, to the above mentioned one, and for use as special applications in the technology of ultrafiltration by membrane filtration. Information as well as the equipment for use in this area is available from Amicon Corporation, Lexington, Mass., and which disclose that the membrane filters they provide are useful with 500, 1000, 10000, 20000 molecular weight cut offs.

Thus, it is shown that these types of ion exchange resins may be used in the ion exchanger of the present invention. Mixture of resins used in the ion exchanger are selected to function with particular impurities which will result from the testing processes for which the device converts the rotary motion imparted to the crank arm 50 from the drive motor 54 into linear motion to drive the pistons 52. The arrangement is such that for every rovolution of the drive motor 54 all sets of dispensing pumps 48–54 will be driven in synchronism.

A set of tubing 18 connects the output of each dispensing pump to one of two alternative positions. FIG. 2 shows typical tubing 18 placed in position in movable holder 16. Holder 16 may be moved from the position shown into a position over a plurality of reaction tubes to which the reagent is to be dispensed as described above.

Additional embodiments of the invention in this specification will occur to others and, therefore, it is intended that the scope of the invention be limited only by the appended claims and not by the embodiments described hereinabove. Accordingly, reference should be made to the following claims in determining the full scope of the invention.

What is claimed is:

1. An improved system for analytical testing for medical purposes comprising a matrix of tubes for reception of serum serum and reagent reagent, means applying a portion of the mixture within the tubes to a spectrophotometer for quantitation, said spectrophotometer being linked to a digital readout device, means passing the mixture from said spectrophotometer through an ion exchanger and membrane filter for final disposition and elimination of pollutants and sediment collection to result in neutralization thereof.

2. The system of claim 1 wherein said ion exchanger and membrane filter receives chemical and biological solutions after use and operation of said analytical testing system.

3. The system of claim 1 wherein said matrix of tubes is provided with samples of blood for multiple medical chemical testing.

4. The system of claim 1 wherein said matrix of tubes are positioned so that the tops thereof are adapted to receive fixed amounts of reagents dispensed by entry ports of a holder, said spectrophotometer is provided with a funnel leading into a flow-through cuvette, and said digital readout device provides a digital readout of concentration.

5. The system of claim 4 wherein said holder has a handle to assist in manually positioning the holder over a row of tubes in said matrix.

6. The system of claim 1 wherein a dispenser container has a selected and specific reagent, tubing connected to the container to a pump which causes the reagent in metered amounts to egress from the container, a syringe pump for receiving the reagent, and a crank arm connected to a motor to drive the pump, said tubing having a valve to prevent backflow of said reagent, and a bypass exit tube for the purpose of readmitting reagent into the container for those operations in which further reagent is not required for tests.

7. The system of claim 1 further comprising a row of syringes positioned over a corresponding row of said matrix of tubes, and means to dispense metered amounts of sera into said row of tubes from the row of syringes.

8. The system of claim 4 wherein said flow-through cuvette leads into a "Y" connection which terminates by emptying into said ion exchanger and membrane filter to purify the waste into a neutral solution for passage into acceptable environmental sewer connections.

9. Method of improved analytical testing for medical purposes comprising arranging a series of tubes into rows forming a matrix each for receiving sera and reagent, applying a portion of the mixture within the tubes to a spectrophotometer for quantitation, recording the result of the quantitation, passing the resultant mixture to an ion exchanger and membrane filter for final disposition and neutralization.

* * * * *